United States Patent [19]
Carrau et al.

[11] Patent Number: 5,330,774
[45] Date of Patent: Jul. 19, 1994

[54] L-MALIC ACID DEGRADING YEAST FOR WINE MAKING

[76] Inventors: Juan L. Carrau, Rua Luiz Michielon, No. 722/102, 95070-Caxias do Sul, RS, Brazil; Aldo J. P. Dillon, Rua Antonia Bohler. No. 79/803, 95070-Caxias do Sul, RS, Brazil; Luciana A. Serafini, Avenue Italia, No. 480, Bairro Sao Pelegrino, 95100-Caxias do Sul, RS, Brazil; Mirian S. Pazqual, Rua Vinte de Setembro, No. 23880/201, 95100-Caxias do Sul, RS, Brazil

[21] Appl. No.: 127,459

[22] Filed: Sep. 27, 1993

Related U.S. Application Data

[63] Continuation of Ser. No. 20,278, Feb. 18, 1993, abandoned, which is a continuation of Ser. No. 585,115, Nov. 20, 1990, abandoned.

[51] Int. Cl.$^5$ .......................... C12N 1/18; C12N 1/00; C12N 1/16
[52] U.S. Cl. ......................... 426/13; 426/15; 435/254.21; 435/255.2; 435/172.1; 935/97
[58] Field of Search ............ 435/255.2, 254.21, 172.1; 935/97; 426/11, 62, 13, 15

[56] References Cited

U.S. PATENT DOCUMENTS

| | | | |
|---|---|---|---|
| 4,472,502 | 9/1984 | Snow et al. | 435/172.3 |
| 5,024,845 | 6/1991 | Thornton et al. | 435/911 |

OTHER PUBLICATIONS

Carrau et al., "Methods for Recovering Fusion Products among Enological Strains of Saccharomyces-Cerevisiae and Schizyosaccharomyces-pombe", Revista Brasil de Genet vol., No. 1, pp. 221-226 1982.

Tamaki, H., "Genetic Properties of Abortive Products Resulting from the Protoplast Fusion in Yeasts Search . . . cerevisae", Proc. Int. Symp. Genet. Ind. Microrganism (4 Meth, 54) 1982.

Kosikov, K., "Comparative Characteristics of 2 remote hybrids produced by Crossing Saccharomyces . . . with pombe"Mikrobiologiya, vol. 52, No. 3, pp. 512-514 1983.

Popov, B., "Preparation and Regeneration . . . Strain Improvement", Zbl. Mickrobiol vol. 141, No. 3, pp. 217-224, 1986.

Primary Examiner—Marian Knode
Attorney, Agent, or Firm—Baker & McKenzie

[57] ABSTRACT

A new Yeast is obtained by fusion of spheroplasts capable of maintaining in a single geno-type the demalifying trait of a Schizosaccharomyces pombe parental strain and the growth rate of the parental strain Saccharomyces cerevisiae. Three more yeasts are obtained from protoplast fusion between the fusion product initially obtained (MB7TCα) and the parental strain, and two other Saccharomyces cerevisiae yeasts. These yeasts are used for obtaining demalification of acid wines.

2 Claims, 1 Drawing Sheet

L-MALIC ACID DEGRADING YEAST FOR WINE MAKING

This application is a continuation of Ser. No. 08/020,278, filed Feb. 18, 1993 which is a continuation of application Ser. No. 07/585,115, filed Nov. 20, 1990 now abandoned.

FIELD OF INVENTION

This invention relates to a new yeast obtained by the fusion of Saccharomyces cerevisiae (Montrachet) and Schizosaccharomyces pombe. The new yeast is effective in degrading L-malic acid during wine making.

BACKGROUND OF THE INVENTION

Four new yeast strains are obtained by: (1) fusion between Saccharomyces cerevisiae (Montrachet) and Schizosaccharomyces pombe; (2) by fusion between the yeast strain formed in (1) above and the parental strain of Saccharomyces cerevisiae; (3) by fusion between the yeast strain formed in (1) above and a yeast with the Killer phenotype; and (4) by fusion between the product formed in (1) above a Saccharomyces cerevisiae denominated as "O Mendoza".

These new yeasts were respectively designated (1) MB7TCα; (2) MBII; (3) MBK; and (4) MBO.

The invention also concerns a process for the reduction of malic acidity in wine making.

A wine is considered acidic when it contains an elevated concentration of L-malic acid, which in turn, is produced by fermentation of musts from not fully ripened grapes. L-malic acid is one of the acids present in musts and wines, together with tartaric acid, citric acid, and much smaller amounts of oxalic acid, uronic acid, succinic acid, lactic acid, acetic acid, glioxalic acid, glyceric acid, pyruvic acid, oxaloacetic acid, alpha-ketoglutaric acid, etc.

The two major acids in terms of concentration, tartaric and malic acids, are metabolized to sugar during the process of grape maturation on the vine. At the end of maturation, malic acid undergoes the greatest rate of degradation, with concentrations being reduced from 200 mEq/l to less than 50 mEq/l, while tartaric acid is degraded from 150-200 mEq/l to 100-150 mEq/l. The metabolization of tartaric acid leads to its lowest concentrations almost one month before the end of grape maturation. Malic acid degradation continues to increase up until full grape maturation. As mentioned earlier, acid musts result from the harvesting of grapes that did not go through the full maturation process. Thus, when fermented, these musts also result in acid wines.

Since tartaric acid present in musts is stable to the action of bacteria and yeasts, the correction of acidity in wines by biological processes is limited to malic acid degradation. Microbial degradation of malic acid can occur through the action of bacteria of the genera Pediococcus, Lactobacillus and Leuconostoc via malolactic fermentation, with the formation of lactic acid, or by degradation to ethanol via the action of yeasts that develop maloalcoholic fermentation.

Malolactic fermentation primarily occurs in wines with acidity of less than 1 g/l tartaric acid and pH higher than 3.1. Fermentation with homofermenting bacteria of highest interest for wine should occur at pH between 3.2 and 3.3 (MENDOZA, 1979).

Schizosaccharomyces pombe yeasts have been used to decrease malic acid in wine by CASTELLI (1969), CASTELLI and HAZNEDARI (1971), BENDA and SCHIMITT (1966), BENDA (1974) HUGLIN et al. (1976), GALANDER (1977) and CARRAU (1981). However, owing to problems related to the growth rate of Schizosaccharomyces pombe which require the use of large inocula for wine fermentation (CARRAU, 1982), the use of this yeast for demalification is not practical for common application in wineries. Indeed, one of the objectives of the present invention was to construct yeasts by fusing spheroplasts of Saccharomyces cerevisiae (having a greater growth rate) and Schizosaccharomyces pombe. These yeasts can solve the problems outlined above because their growth rate is more rapid than that of the parental strain Schizosaccharomyces pombe and because they express the ability to degrade L-malic acid in addition to presenting part of the genome of yeasts traditionally used in wine fermentation.

A decrease in malic acid content also favors the natural development of malolactic fermentation which is known to be a determinant of the biological stabilization of wines.

The present invention was based on the use of microbial genetics, to whose methods protoplast fusion was added during the 1970's. This method permits the exchange of genetic material between cells that are not compatible for crossing. For yeasts, protoplast fusion utilizes lytic enzymes from the digestive juice of Helix aspersa which produce the formation of cells fully (protoplasts) or partially (spheroplasts) devoid of walls. Both protoplasts and spheroplasts can be easily fused in the presence of polyethylene glycol, as initially observed by VAN SOLINGEN and VAN DER PLATT (1977). The fusion products are then submitted to conditions that will lead to the reestablishment of the cell wall. These conditions include a regenerating medium containing $Ca^{++}$ and a large osmotic concentration, with inoculation onto pour-plates yielding the best percentage of regeneration. This technique has been used previously to obtain fusion products of technological interest (RUSSEL and STEWART, 1979; TUBB, 1979). Modern wine making outfits use selected yeasts that are applied to the fermentation by the use of starter. Carrau (1982) reported the demalifying ability of six different strains of Schizosaccharomyces pombe, which degraded 55 to 75% of malic acid within twenty-four hours and 83.8% to 98.8% after seventy-two hours. On the basis of this ability of Schizosaccharomyces pombe to degrade malic acid, (CARRAU, 1979) proposed large-scale fermentations using this yeast to degrade malic acid in wine. This process would utilize inocula of $500 \times 10^5$ cells of Schizosaccharomyces pombe in order to obtain partial malic acid degradation during wine fermentation.

SUMMARY OF THE INVENTION

The reduction of L-malic acid during the fermentation of a wine can be effectively achieved by the introduction of the new yeast formed by the fusion of Saccharomyces cerevisiae (Montrachet) and Schizosaccharomyces pombe (Benda I). The fusion product is designated as MB7TCα.

DETAILED DESCRIPTION OF THE INVENTION

Figure 1:
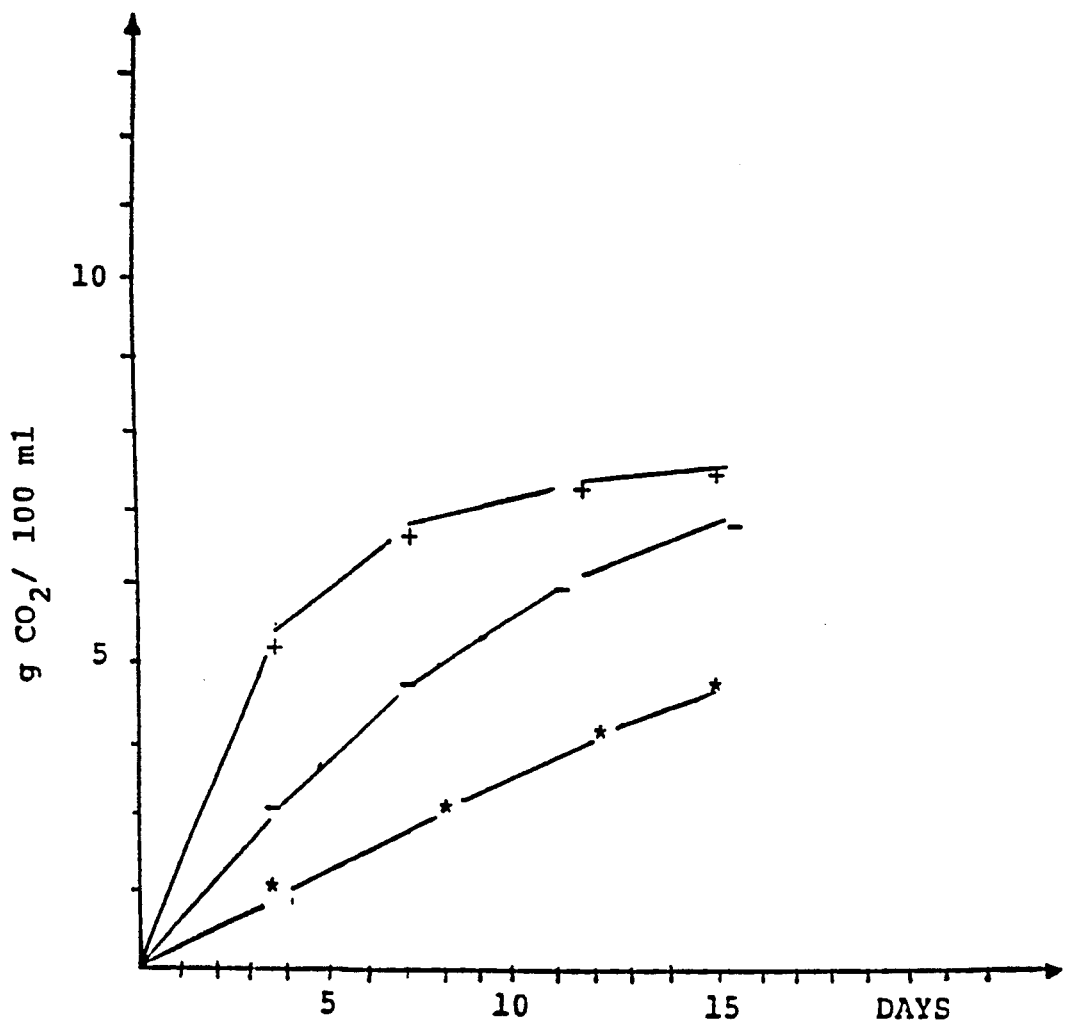
FIG. 1 is a cartesian coordinate plot of the fermentation rates of MB7TCα, the Montrachet and Benda I strains.

The methodologies that constitute the inventions are reported below:

1. Selection of Genotypes to Obtain the First Fusion Product (MB7TCα)

A strain of *Schizosaccharomyces pombe* called Benda I was selected as the yeast with the most effective ability to degrade malic acid. As a yeast of enologic use which produces good organoleptic characteristics in wines, we selected the strain *Saccharomyces cerevisiae* denominated Montrachet.

2. Selection of Markers for Obtaining MB7TCα

The *Schizosaccharomyces pombe* strain does not grow on galactose as the single source of carbon and its growth on WLN (Difco) gives origin to greenish colonies. The Montrachet strain of *Saccharomyces cerevisiae* forms white colonies when growing in WLN medium.

3. Production of Spheroplasts

This invention was based on the technique of GOODEY (1980), except that 0.8M KCl was substituted for 1M sorbitol as osmotic buffer.

4. Spheroplast Fusion and Regeneration

After the appearance of spheroplast levels higher than 85% in the two suspensions, the latter were concentrated by centrifugation and the pellets pooled in a single tube and treated with 2 ml of a solution of 37% polyethylene glycol 4,000 (GOODEY, 1980).

5. Recovery of Fusion Products

After the fusion treatment, the cells were regenerated in regenerating medium (6.67 g YNB, 20 g glucose, 180 g sorbitol, 1.11 g $CaCl_2$, and distilled water to 1,000 ml).

The colonies formed were observed microscopically to determine the occurrence of colonies with irregular borders, called "hairy" colonies. Colony coloration was also observed in WLN medium and colonies with irregular borders that also showed colors differing from those of the parental strains in WLN were studied for capacity to degrade malic acid.

6. Production of MBO, MBII and MBK

In order to increase the genotypic contribution of Saccharomyces to the fusion products, strain MB7TCα was fused with strains O Mendoza and KI, both of them *Saccharomyces cerevisiae*, and also with the parental strain Montrachet.

The methods for obtaining new fusion products were the same as those described for MB7TCα.

7. Evaluation of Demalifying Ability

The clones obtained by spheroplast fusion were studied in test tubes and in 1,000-ml Erlenmayer flasks containing grape must. A racemic mixture of malic acid (10 g/l) was added to the musts for the study of malic acid degradation ability. The results for clone MB7TC with respect to fermenting ability, as indicated by $CO_2$ release with the use of Müller valves by the method of CASTELLI (1969), and malic acid degradation are shown in Figure I and Table I, respectively. It can be seen that the fermenting rate of MB7TCα is higher than that of the parental Schizosaccharomyces pombe strain, and that its demalifying ability is good.

8. How These Fusion Products Can Be Used By the Wine Making Industry

In wine making, the concentrations of native yeast cells after the extraction of grape juice often reach values higher than $10^6$ cells/ml, a fact implying that the yeasts described in the present invention need to be inoculated at similar concentrations for their demalifying ability to be expressed. The present invention proposes a wine making process utilizing inocula of $100 \times 10^5$ cells/ml fusion products at the beginning of fermentation in order to obtain wines with partial degradation of L-malic acid.

A deposit of the strain of the present invention has been made under the Budapest Treaty on Jan. 15, 1990 as DSM 5736 at the following international depositary authority: DSM DEUTSCHE SAMMLUNG VON, MIKROORGANISMEN UND ZELLKULTUREN GmbH, Mascheroder Weg 1 B, D-3300 Braunschwieg, Germany.

TABLE I

Malic acid degradation by the fusion product MB7TC$^{\alpha}$ and the parental strains Montrachet and Benda I, expressed as mEq/l and % total.

| Strains | 72 hours | | 144 hours | |
|---|---|---|---|---|
| | mEq/l | % | mEq/l | % |
| Montrachet | 0 | 0 | 0 | 0 |
| Benda I | 47 | 70 | 48 | 72 |
| MB7TC$^{\alpha}$ | 25 | 37 | 55 | 81 |

We claim:

1. A biologically pure culture of a yeast strain obtained by the fusion of *Saccharomyces cerevisiae* (Montrachet) and *Schizosaccharomyces pombe* (Benda I), the yeast strain having all the identifying characteristics of DSM 5736 as deposited with the international deposit authority known as DSM Deutsche Sammlung Von Microorganismen Und Zellkuturer GmbH.

2. A method for reducing L-malic acid during wine fermentation, the method comprising:
inoculating the wine with at least $100 \times 10^5$ cells of a yeast strain per milliliter of wine, wherein the yeast strain is MB7TCα and is deposited as DSM 5736 with the international deposit authority known as DSM Deutsche Sammlung Von Microorganismen Und Zellkuturer GmbH.

* * * * *